US 8,689,650 B2

(12) United States Patent
Villarreal V et al.

(10) Patent No.: US 8,689,650 B2
(45) Date of Patent: Apr. 8, 2014

(54) IMMERSIBLE OXYGEN SENSOR FOR MOLTEN METALS

(75) Inventors: Ascencion Z. Villarreal V, San Nicholas de los Garza (MX); Paul A. Turner, Milwaukee, WI (US)

(73) Assignee: Heraeus Electro-Nite Co., LLC, Langhorne, PA (US)

( * ) Notice: Subject to any disclaimer, the term of this patent is extended or adjusted under 35 U.S.C. 154(b) by 226 days.

(21) Appl. No.: 13/167,081

(22) Filed: Jun. 23, 2011

(65) Prior Publication Data

US 2011/0271737 A1 Nov. 10, 2011

Related U.S. Application Data

(63) Continuation-in-part of application No. 13/129,678, filed as application No. PCT/US2009/041859 on Apr. 28, 2009.

(51) Int. Cl.
*G01N 1/12* (2006.01)
*G01N 1/00* (2006.01)
*G01N 33/20* (2006.01)

(52) U.S. Cl.
USPC .......................... 73/864.55; 73/19.07; 73/863

(58) Field of Classification Search
USPC ........................ 73/19.07, 863, 863.71, 864.55
See application file for complete search history.

(56) References Cited

U.S. PATENT DOCUMENTS

| 4,358,630 | A | 11/1982 | Falk |
| 4,557,152 | A | 12/1985 | Plessers et al. |
| 4,699,014 | A | 10/1987 | Boron |
| 4,881,824 | A | 11/1989 | Falk et al. |
| 4,964,736 | A | 10/1990 | Cure et al. |
| 5,591,894 | A | 1/1997 | Falk |
| 5,772,324 | A | 6/1998 | Falk |
| 5,911,269 | A | 6/1999 | Brander et al. |
| 5,975,755 | A | 11/1999 | Roberson |
| 6,139,180 | A * | 10/2000 | Usher et al. ................ 374/1 |
| 6,216,526 | B1 | 4/2001 | Junker et al. |
| 7,141,151 | B2 | 11/2006 | Habets |
| 2001/0020397 | A1* | 9/2001 | Cappa et al. ............ 73/864.58 |
| 2011/0219889 | A1 | 9/2011 | Villarreal V et al. |

OTHER PUBLICATIONS

Office Action issued Apr. 25, 2013 in U.S. Appl. No. 13/129,678.
Office Action issued Sep. 19, 2013 in U.S. Appl. No. 13/129,678 by Villareal V.

* cited by examiner

*Primary Examiner* — Hezron E Williams
*Assistant Examiner* — David Z Huang
(74) *Attorney, Agent, or Firm* — Panitch Schwarze Belisario & Nadel LLP

(57) ABSTRACT

An improved immersible oxygen probe for molten metals has a gas permeable body including an immersion end and a support end adapted for being supported by a lance. An oxygen cell and a thermocouple are supported in the immersion end of the body. An unobstructed gas flow passageway is provided through the gas permeable bodies and through the probe body from the immersion end to the support/connector end whereby gases released from the molten metal and sensor body during immersion readily pass through the probe and can escape from within the probe. Thus rapid analysis of the molten metal with improved accuracy within a few seconds after immersion is achieved. The probe contains a sample mold at least partially positioned in an unconfined portion of the permeable body.

3 Claims, 5 Drawing Sheets

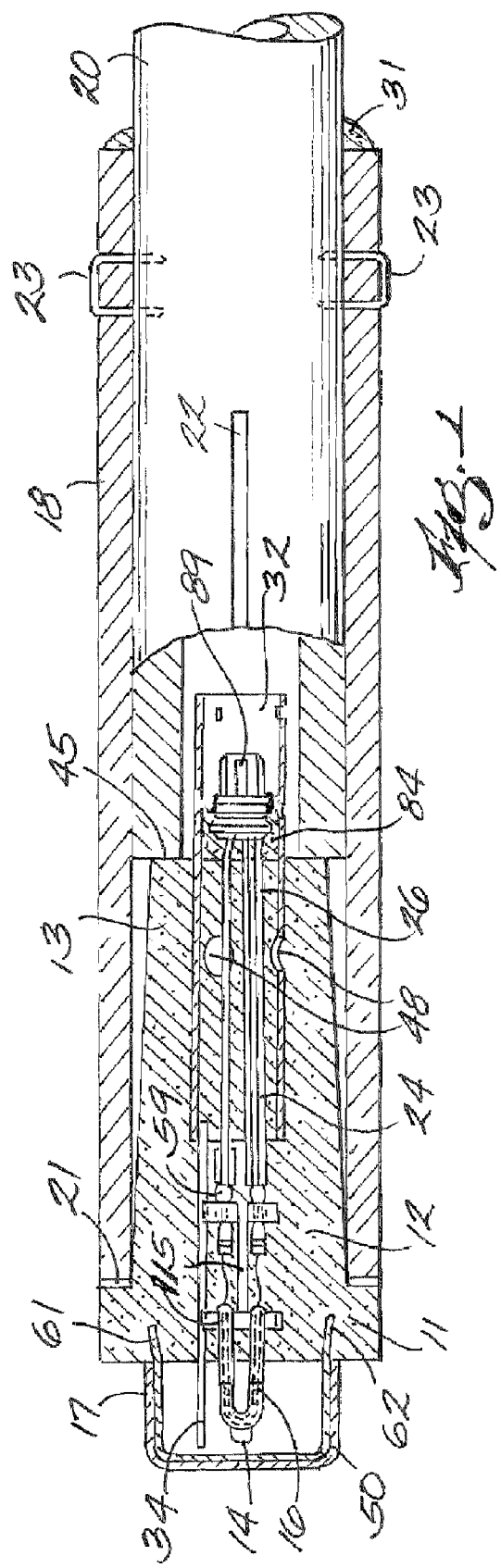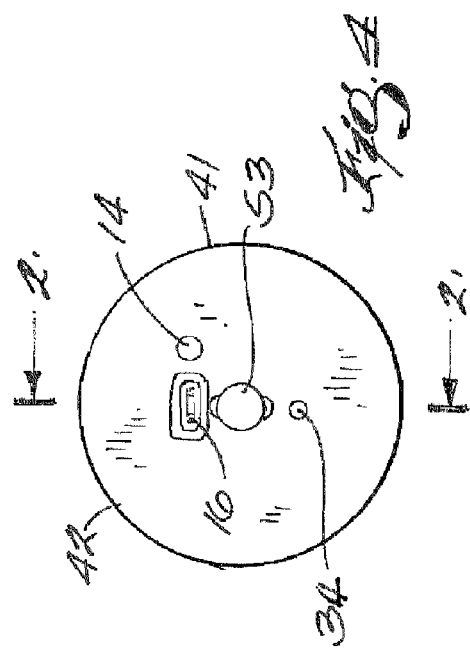

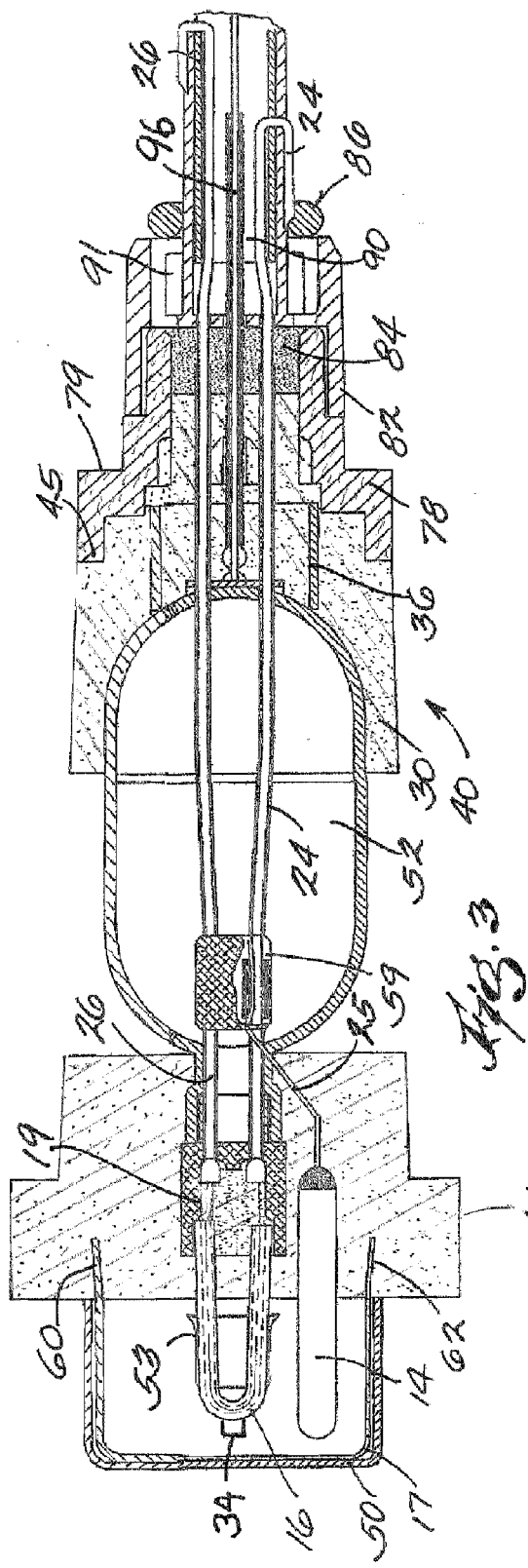
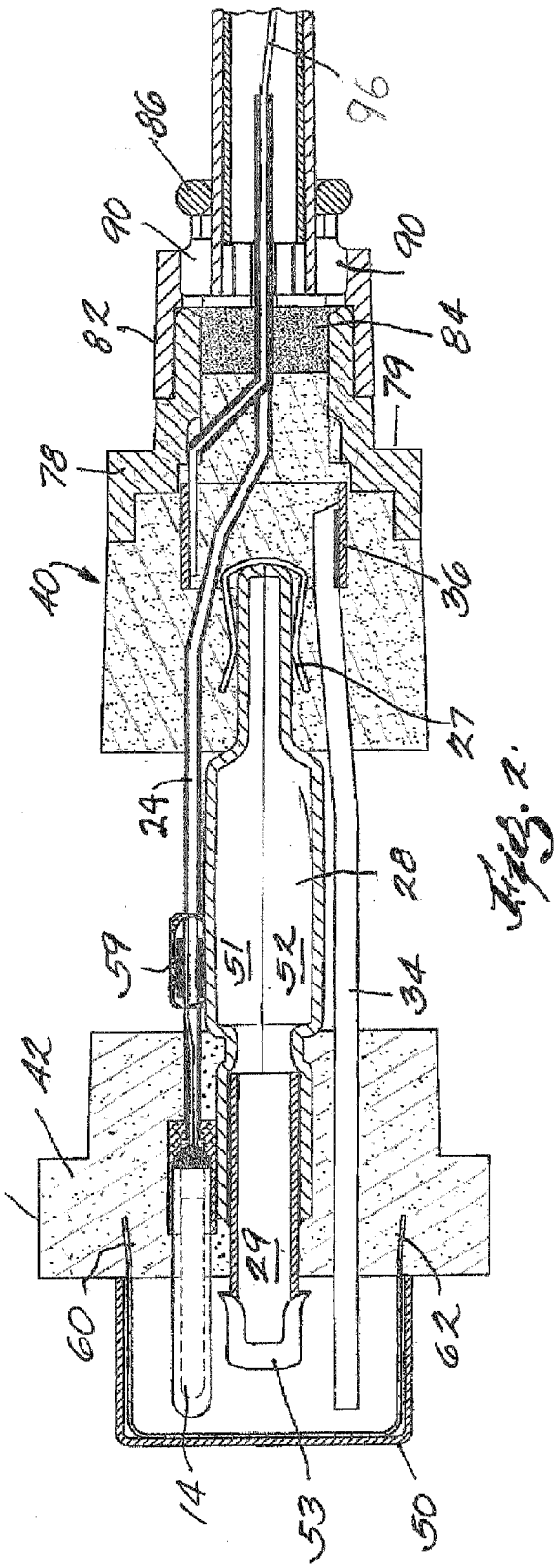

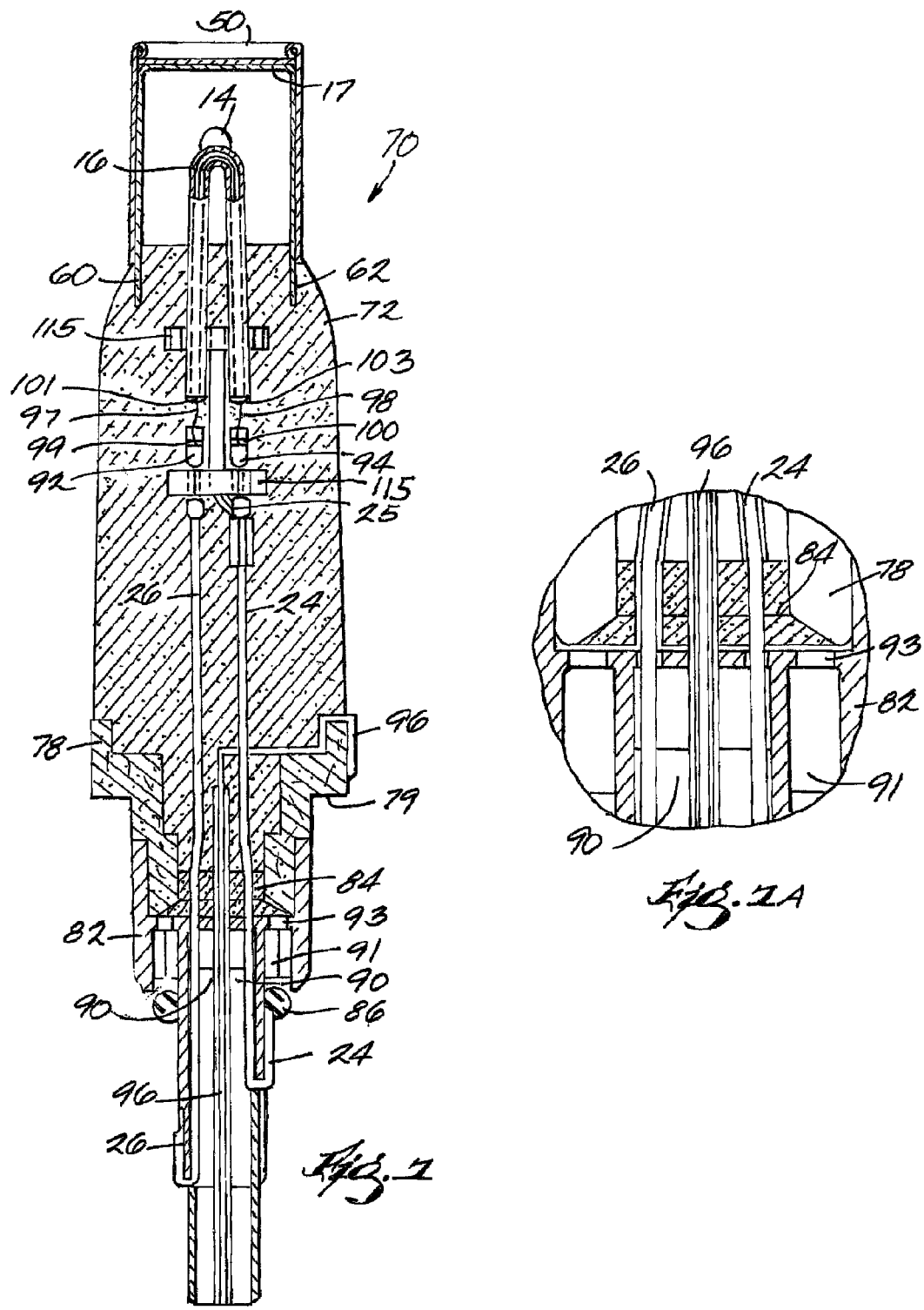

IMMERSIBLE OXYGEN SENSOR FOR MOLTEN METALS

This application is a continuation-in-part of U.S. patent application Ser. No. 13/129,678, filed 17 May 2011, claiming priority to PCT Application No. PCT/US09/41859, filed 28 Apr. 2009.

FIELD OF THE INVENTION

This invention relates to immersible probes for measuring and sampling selected characteristics of molten metal, especially molten iron or steel. The probes are used to measure the temperature and oxygen content of a molten metal and in accordance with some embodiments, are provided with a sample mold so that they may be used to retrieve, simultaneously with those measurements, a representative, high quality sample of the metal for chemical or spectrographic analysis. The probes of this invention can combine all of said devices in a single probe but may include two or even a single measuring device, if desired.

BACKGROUND OF THE INVENTION

Immersible oxygen and temperature measuring probes, usually supported for immersion by a molten metal consumable, ablative paperboard tube attached to a sensor and covering and protecting a support pipe or lance that carries the sensor electrical leads. Such lances have been used for at least half a century. In recent decades the probes have often contained a stabilized zirconia oxygen cell and a platinum-rhodium immersible thermocouple. Some such probes have included a sand filling but have included one or more gas impermeable components such as ceramics, plastics, potting cements, silicones or the like in their designs believed to be necessary to protect the measuring devices from unwanted exposure to heat, pressure, hot gases and hot gas movements. Such gas-contact preventing components were heretofore thought to be a necessary protective feature of the oxygen and temperature measurement systems in view of the high temperature melts involved, typically 3000° F. or 1700° C., even though immersion times are limited to about 10 seconds.

Notwithstanding the long history of use of thermocouple and oxygen probes, which sometimes include a metal sampling mold, such probes have heretofore sometimes been subject to fluctuating readings and thus are unable to consistently provide the quick, accurate, repeatable oxygen content and temperature readings required for today's demanding manufacturing processes. The interruption, pressurization and restraint of the movement of even trace amounts of combustion products or moisture emanating from paperboard or from coatings or materials used in the probe or gases dissolved in the melt and existing in the probe often result in errors in the readings, often causing the need for retesting thereby interrupting and increasing production time and therefore increasing production costs. To date, combination immersion testing, sampling and oxygen content determining devices have been found to perform with inadequate speed and inconsistent accuracy. In light of these shortcomings, a need has continued to exist for improved probes and testing devices.

SUMMARY OF THE INVENTION

The present invention provides improved metallurgical immersible measuring devices by utilizing gas permeable design and components and wherein the measuring devices and related components are preferably all baked together into a gas permeable baked sand-resin structure. Additional features also emphasize increased venting of the devices and elimination of gas flow blockages and pressure surges which may interfere with reading accuracy in previous devices. Test devices in accordance with the invention are able to provide accurate readings in parts per million within seconds after immersion. Gases can flow into or out of the probe virtually instantaneously, even through the immersion, measuring end thereof, so that pressure surges are eliminated that could otherwise adversely affect the accuracy of the readings.

Utilizing the pressure of hot gases escaping from the melt, the probe bodies provided by the invention perform in a manner similar to a vented chimney. While it will be understood that the stabilized zirconia oxygen cells commonly used depend on electron transfer and themselves are entirely gas impermeable and gas tight, the configuration of the probe is constructed from gas permeable materials and/or voids or open spaces internal to the gas permeable body that allow a free gas flow throughout and through the probes. Thus internal probe temperatures arrive at an equilibrium rapidly and pressure variations or surges are minimized in gas containing parts.

Briefly, the invention provides an improved immersible oxygen probe, in some cases with a sample mold, for molten metals having a gas permeable body portion including an immersion end and a support end adapted for being supported by a lance. The immersion end is preferably devoid of gas impermeable components with the exception of the measuring devices used, themselves, and a temporary capping system. The latter includes a combustible outer cap and inner fusible metal caps. Measuring devices, usually, an oxygen cell and a thermocouple are supported exclusively by the gas permeable body. The probe includes the testing devices in the immersion end for reading the oxygen content, temperature and in some embodiments retrieving a sample of the molten metal bath. An unobstructed gas flow passageway is provided through the gas permeable vehicle body and through voids, if any, in the probe body for gas flow from the immersion end to the support/connector end whereby gases released from the molten metal and probe during the immersion of the immersion end can easily escape from within said probe. Thus rapid analysis of the molten metal within a few seconds after immersion is achieved providing consistent nonfluctuating readings of temperature and oxygen content.

The probe according to the invention includes a gas permeable body which preferably is of an annular shape formed of baked sand-resin or other particulate material that can be formed into a gas permeable body. In one preferred embodiment, the permeable body is provided with a protruding shoulder adjacent to the immersion end with the annular shape otherwise adapted to fit within a supporting paperboard sleeve. The shoulder serves as a stop member for abutment by an end of a paperboard sleeve. In a preferred embodiment, the support end is also provided with either a reduced diameter continuation of the annular body, or with a separate gas permeable body in the event that a metal sampling mold is included within the probe. In accordance with alternate embodiments, a protruding gas permeable shoulder is not used, but alternative means are provided to act as a stop and gas tight seal for the supporting ablative sleeves.

In accordance with a modified embodiment, the sampling mold is mounted within a gas permeable body which may be held within a supporting tube, usually of paperboard in a manner so as to protrude all or in part out of the supporting tube in the immersion direction. This provides a structure wherein the sampling mold & a sample contained therein is readily removed from the probe body, usually by striking against a hard surface or striking by a tool such as a hammer.

The sand-resin material may include 2 weight % or more of a resin (approximately 5 weight % resin in a preferred embodiment) and approximately 5 weight % ferric oxide. The ferric oxide can alleviate any unwanted RF interference during use of the probe. In accordance with preferred embodiments, no coating nor metal plating is used on the interior of any metal caps used in the vicinity of or in the immersion end of the probe in order to avoid any possible unwanted distortion of the data provided by the probe. However, coatings or metal plating that do not have a deleterious impact on the probe can be used if desired. It is also preferred that there be no holes or openings in any metal caps used.

In order to avoid the formation of a residual metal ring after the melting of the metal caps, it is preferable to use an irregularly shaped edge or protruding pins are used on the portions of the caps that become embedded in the sand-resin body. In an alternative version of the embodiment, a ledge of sand-resin material is molded onto the face of the probe and acts as a press-fit feature for the metal capping. The presence of this feature prevents the formation of a residual metal ring post immersion. Metal capping systems are mounted without cement and with the irregular shaping or pins at the sand contact area which will avoid formation of round shapes or rings existing after the capping system has melted. An electrical ground consisting of a single point rather than a ring or other structure is greatly preferred.

In versions that include a sample mold, necessary quick release of the mold and sample from the probe body is enhanced by use of spaces or voids in the sand-resin body or use of a sand-resin blend near the connector end that produces a readily frangible material, for example by reducing the amount of resin in the blend. In embodiments that utilize two different sand blends without employing a void in the sand-resin body, the mating interface between the two sands acts as a fault line or weak point, facilitating removal of the sample. Likewise, metal clips on the mold body are not preferred and are avoided if possible. Release of the mold can also be facilitated by use a larger particle size resin-sand. Any other particulate or fibrous material that is uniformly sized, high temperature, inorganic, gas permeable and moldable may be used. It is important that the exterior and interior of the immersion end of the probe body be free of any cements, sealing compounds, combustibles, moisture and adhesives, all of which might impede the free gas flow into and through and throughout the probe.

BRIEF DESCRIPTION OF THE DRAWINGS

FIG. 1 is a longitudinal sectional view of a measuring probe of the invention of a type including an oxygen sensor and a thermocouple showing a pair of supporting/venting loose fitting paperboard tubes adapted to be supported by a lance.

FIG. 2 is a longitudinal sectional view of a measuring probe of the invention of a type including a sampling mold in addition to an oxygen sensor and thermocouple.

FIG. 3 is a longitudinal sectional view of the probe of FIG. 2 shown from a different viewing angle offset at right angles from FIG. 2.

FIG. 4 is an end view (not to scale) showing the immersion sensor end of the probe of FIGS. 2 and 3 with cap 17 removed.

FIG. 7 is a longitudinal sectional view of a probe of FIG. 6.

FIG. 7A is an enlarged view of the connector/venting area of the probe of FIG. 7.

DETAILED DESCRIPTION

Figure 6:
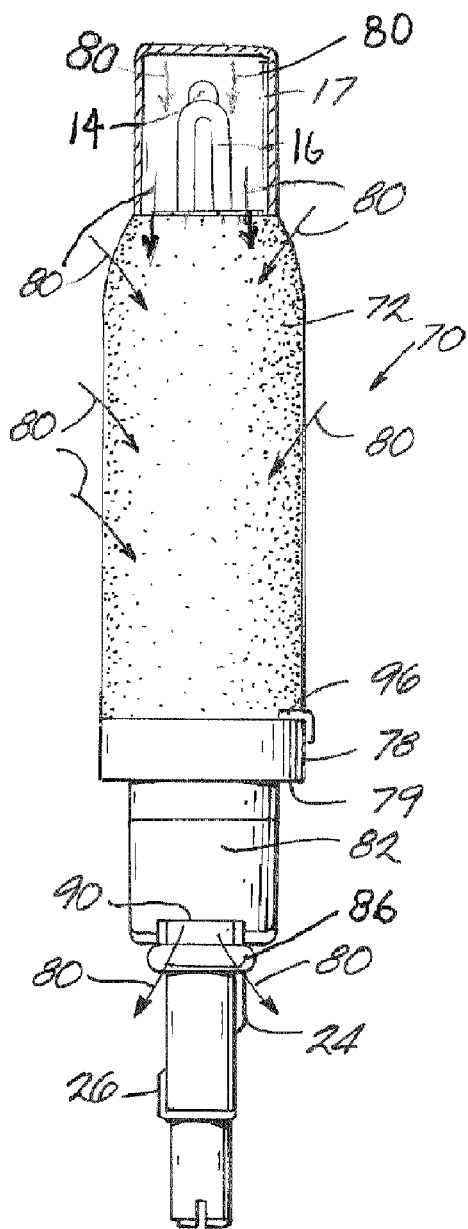
FIG. 6 is a longitudinal view of a probe in accordance with another alternative embodiment with a temporary cap partly cut away, illustrating gas flow into, through and out of the gas permeable probe body.

In accordance with the embodiment of the invention shown in FIG. 1, probe 10 includes a first gas permeable sand-resin, generally cylindrically shaped body 12 formed of a baked gas permeable sand-resin mixture. As shown, the baked sand-resin body 12 has a stem portion 13 of a size adapted to fit within the interior of paperboard sleeve 18 and a radially raised or enlarged portion 11 which serves as a stop for the immersion end of paperboard sleeve 18. The abutting surfaces of the sand-resin body 12 and the end surface 45 of the paperboard sleeve 18 should be totally sealed gas tight. Thus a ceramic cement 21 or the like is used between these abutting surfaces. The end surface 45 is abutted by the end of smaller tube 20 but it is not adhered thereto. Any other sand body contact with the paper tubes 18 or 20 internal to the tubes should not be gas tight. Tubes 18 and 20 are loosely fitted in order to allow gas flow there between. The embodiment of FIG. 1 (as well as FIGS. 6 and 7) is used in instances wherein only the oxygen content and temperature of the melt is to be determined.

Figure 5:
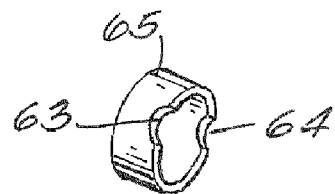
FIG. 5 is a perspective view of an alternative cap having an irregular scalloped end surface that avoids formation of metal rings when melted during immersion of the probe.

In FIG. 1 and all figures except FIG. 5 that show the tip portion 14 of an oxygen measuring cell, usually a stabilized zirconia oxygen cell can be seen in the drawings together with a quartz U-tube loop portion 16 of a thermocouple assembly and Pt/Rh wires which are welded to conductors 24 and 26 and directly encased in the sand body and connected to monitoring instrumentation. A small ceramic basket 19 also supports the quartz loop 16. The welds are the thermocouple cold junctions 99 and 100 and are best shown in FIG. 7. They are not shielded, but instead enclosed in the well vented sand body in accordance with the present invention. The outer surface (internal to the sand body) of the zirconia oxygen cell 14 (also see FIG. 3) internal to the gas permeable sand is totally exposed in all areas to the sand-resin body 12. The smaller diameter paper tube or sleeve 20 is adapted to be supported by the immersion end of a support pipe or lance of standard configuration. The inner, smaller tube 20 has an outer diameter about the same as that of a reduced diameter end portion 13, 45 of probe body 12.

A slot or slots 22, best seen in FIG. 1 are provided in the distal end of the sleeve 20 to allow escape of gases from the interior area of sleeve 18 into the interior of the smaller diameter sleeve 20 from whence the gases can escape to the atmosphere either directly or between the loosely fitting tubes, lance or support pipes. As previously noted, sleeve 20 fits loosely within the interior of larger sleeve 18 to facilitate escape of gases. Sleeves 18 and 20 can be stapled together, 23, to stabilize the assembly. Also a gas vented 360 degrees interrupted circle of adhesive 31, FIG. 1, may be applied around the perimeter of tubes 18 and 20 at the proximal end of tube 18 to allow venting through this area. A metallic connector tube 32 is attached to a steel ground rod or wire 34 that extends into the immersible tip portion of the device as shown. The heavy structural ground rod may be pointed in the area exposed to the molten metal to ensure a fine single point grounding and to avoid possible ground rod dilution and contamination of the sample. In order to further enable venting of gases, one or more openings 48 are provided through the connector and ground tube 32. See FIG. 1. Tube 32 may have a diameter of about ⅜ inch (1 cm).

The connector system used and well vented as shown in FIG. 1 is commonly known and defined as a ⅜ inch pipe sized connector system. The vented connector system used in FIGS. 2, 3, 6, 7, and 7a are commonly known and defined as a ¾ inch pipe size connector system. A metal sample mold 28, formed by halves 51 and 52, having a immersible fused quartz sample mold filling tube 29 covered by a small metal cap 53 is included in the embodiment 40 of FIGS. 2, 3 and 4. As most clearly shown in FIG. 2, sample mold 28 is of a conventional two-part clam-shell configuration common in the art which includes halves 51 and 52 and a quartz fill tube 29 through which the molten metal can enter during immersion. A steel clamp 27 may be used, if preferred, to hold the two mold halves together. Quartz sample tube 29 may be provided with a fusible steel cap 53. Also seen in FIGS. 2 and 3 is ground rod or wire 34 which, as in the case of probe 10 of FIG. 1, ensures that the electrical potential of tube 36 is grounded at single point relative to the molten metal bath when it is contacted by the rod 34. Mold 28 and ground rod 34, swage 59 and metal tube 36 provide a prebaking structural integrity to the probe prior to the baking of the sand body.

Thus greater physical strength is provided to the mold combination of FIGS. 2 and 3 to better withstand the forces necessary to submerge the probe deeply into a dense metal melt. Since the sensor combination with sample mold 28 displaces a greater volume of the melt, a greater immersion force is required. In order to obtain excellent metal samples a substantially instantaneous evacuation of gases from within the mold is required so that the molten metal can enter the mold in the brief time available.

The single point ground rod or wire 34 may be exposed as in FIG. 2 or may be located in any area that is preferred at the surface of the immersion sensor that will be exposed to the molten metal. Also see ground wire 96, FIG. 7, for another alternate example of ground point exposure.

The venting of the immersion sand sensor system through the paper tubes and connector system is substantially completely gas permeable, instantaneous, with no detectable back pressure.

As also best seen in FIGS. 2 and 3, oxygen cell 14 utilizes a circuit formed by the ground rod 34 and a positive lead 24 of the thermocouple U-tube 16, to which a positive lead 25 for the oxygen cell is swaged at junction 59, so that only three leads are necessary to enable operation of the thermocouple 16 and the oxygen sensor 14. As seen, the immersion tip is covered by a consumable slag repelling paper cover 50 which covers the fusible metal end cap 17. Cap 17 preferably has no openings in it and the measuring components, sample tube 29 and ground 34 thus can be covered and protected until immersion. Cap 17 is preferably formed from non-galvanized steel so that, for example, the presence of zinc vapors in the areas of the oxygen cell are avoided. A thin metal cap with only outer surface corrosion protection can be used. Metal caps 17 or 65 are preferably mounted without cement and are provided with irregular shaping such as scallops 63, 64 at the sand-resin contact area of cap 65 as seen in FIG. 5 or alternatively with pins 60, 62 as shown on cap 17 in FIGS. 1, 2, 3 and 7. This results in avoidance of the formation of a residual ring remaining after the molten metal exposed capping system has melted which could cause electrical interference with the sensor measurement signals when used in induction or electric melting furnaces or electric reheating ladles. Metal rings are thus avoided except in the connector end or area. The connector ends are provided with mating electrical connectors of known design, except for the venting, for providing means for transmitting data from the testing devices of the probe to remote electronic monitoring equipment.

The embodiments of FIGS. 2 and 3 are intended for use with a pair of paperboard tubes 18 and 20 similar to those shown in FIG. 1. The gas permeable body 42, having a stem portion and provided with a projecting shoulder 41 which, in similar fashion to the embodiment of FIG. 1, serves to limit the distal movement of tube 18 to which it is adhered forming a gas tight seal. Stem 43 is adapted to closely fit within the tube 18 and the proximal end 45 of the separate permeable sand-resin body 30 may serve as a stop for the smaller tube 20 which is preferably also provided with a slot 22 (seen in FIG. 1) to provide optimal gas escape from within the probe body into a supporting lance or directly to the atmosphere. Alternatively, a connector 78 supports the end of body 30 as illustrated in FIGS. 2 and 3. Connector 78, which may be formed of a ceramic material, is provided with a shoulder 79 to which tube 20 may be abutted but preferably not adhered at the abutment. The distal end of the outermost tube 18 is adhered gas tight to its abutting surface but, to preserve venting, the inner tube 20 is not adhered gas tight to any of the sand body embodiments of the invention illustrated herein.

In the embodiments of FIG. 1 and of FIGS. 2 and 3 which utilize two supporting tubes 18 and 20, several alternative avenues are provided for the flow of gases out of the probe body. Unlike previous devices, the described devices allow the greatest amounts of gases entering the probe body to enter through the most deeply immersed distal end of the probe, adjacent to the measuring instruments, temperature and oxygen which both, of course, have components that are necessarily not gas permeable. The gases are then able to flow between the probe body and the larger tube 18 as well as between the tubes 18 and 20 into the area of slots 22. In the embodiment of FIG. 1, gases can also flow through a ceramic fiber filter 84 and around the plastic electrical connector 89. Connector 89 is loosely secured by small projections, often referred to as "nubs" in the interior of tube 32. In the embodiment of FIG. 1, gases also exit through metal tube 32, through filter 84 and around plastic electrical connector 89 into the space between tube 20 and the supporting lance (not shown) and into the atmosphere. In the embodiment of FIGS. 2 and 3 a similar venting path is also available. In the embodiments, such as FIG. 1 and FIGS. 2 and 3, that have two paperboard tubes 18 and 20, gases also vent from between the two tubes out through intermittent openings in adhesive junction 31. In the case of FIGS. 2 and 3, the outer diameter of sand-resin body 30 is less than the inner diameter of tube 18 in order to allow free venting in the space between them as well as through the gas permeable probe bodies 12 and 42.

The probes of this invention 10, 40 and 70 are formed by assembling all of the illustrated components in a mold together and vibrated with a baking sand-resin mixture used to form each of the gas permeable parts 12, 30, 42 & 72. Each such assembly is then baked at approximately 500° F. (260° C.) in order to form the gas permeable sand-resin body with the other components baked in situ and held together in place by the resultant strong porous body. Foundry sand having a particle size of about 50 to 100 mesh, as desired may be used. Sand-resin material comprises approximately 5 weight % resin and approximately 5 weight % ferric oxide has been found suitable with especially preferred uniform particle sizes of 70 to 90 mesh, but other sized particles can be substituted so long as the desired gas permeability, strength and sample release is provided. The sand-resin material may include 2 weight % or more of a resin (approximately 5 weight % resin in a preferred embodiment) and preferably approximately 5 weight % ferric oxide. The ferric oxide can alleviate any unwanted RF interference during use of the probe. In accordance with preferred embodiments, no coating nor metal plating is used on any metal caps used in the vicinity of or in the immersion end of the probe in order to avoid any unwanted distortion of the data provided by the probe. It is also preferred that there be no holes or openings in any metal caps used. While sand-resin mixtures are greatly preferred formation of the permeable probe bodies of the invention, it will be understood by those skilled in the art that other materials can be substituted, for example, resin blends with sized inorganic gas permeable materials or comminuted particles of inorganic materials other than sand.

The sand-resin materials preferably used in forming the probes of this invention are commercially available from various foundry sand suppliers and are variously referred to as "resin sand" or "binder coated sand." Due to sand being the main ingredient of the probe bodies of this invention, however, they are referred to herein as "sand-resin" compositions. Numerous resin binders are used in the foundries. Some of these are low temperature curing systems which could be utilized. However, it is greatly preferred that curing of the probe bodies of the invention be conducted at elevated temperatures of at least 350° F. (176.67° C.), and preferably 500° F. (260° C.) in order that a minimum amount of volatile residues (i.e. volatile at highly elevated temperatures of molten steel) remain in the bodies after curing. Examples of suitable resin systems are epoxide, epoxide novolac, furane, amine-hardened resins and thermosetting resins such various urea formaldehyde systems. Such materials will be selected by those skilled in the art based on characteristics of gas permeable bodies produced by curing of the same.

Referring to FIG. 4, there is shown an end view (not to scale) of the probe of FIGS. 2 and 3. It has been found necessary, in the case of each of the embodiments of the invention, that no part of the stabilized zirconia oxygen cell 14 be closer to the quartz thermocouple tube loop 16 than 0.2375 inch (0.60 cm).

Referring to FIGS. 6-7, there is seen another alternative probe 70 of the invention in which the gas permeable probe body 72 does not include an outwardly extending flange such as 11 of FIG. 1, or of 41 of FIGS. 2 and 3, but instead has a generally smooth profile. The immersion tip profile may be varied as desired, for example, cylindrical square or oval rather than the tapered shape illustrated. Gas flow into and out of the probe 70 is symbolized by arrows 80. Unlike previous probes, gases are able to flow into the distal, immersion end surfaces of the probe body as indicated by arrows 80. Thus, gases from the melt flow into, through and throughout the described probe bodies. In this modified embodiment of FIGS. 6 and 7, a shorter and thinner ground wire 96 is provided.

A ceramic connector base 78 is provided with a shoulder 79 which serves as a gas impermeable stop against which an end of a supporting paperboard tube of type 18 of appropriate length and diameter can be adhered. These parts may be supported in a plastic outer connector 82. This connector has a plurality of openings 93 (see FIG. 7A) which allow gas flow out of the probe through the open interior 91 of connector 82 and out of channels 90. The openings 93 and structure of connector 82 also retain a fibrous filter layer 84 that forms a filter for trapping impurities carried by the gases. As shown in FIGS. 7 and 7A, a plastic or elastomeric gasket or O-ring 86 prevents impurities from entering associated electrical components. Thus moisture or other contaminants containing gases such as tars, sand particles, etc., are prevented from moving through the venting system formed by the probe. Channels 90 are in the form of two or more intermittent openings around the circumference of the proximal end of connector 82. The plastic or elastomeric O-ring gasket 86 does not interfere with the air flow channels 90 which allow escape of gases from the probe body, but serves to seal the end of any subsequently attached connector in which electrical components are contained thereby protecting them from poor performance or damage which could be caused by entrance of contaminants. The fibrous filter layer 84 may be formed of refractory fibers, such as tightly packed high alumina fibers, and has been found to protect the connector systems and electrical components from damage caused by gas borne volatiles, contaminants and moisture.

As best seen in FIG. 7, probe 70 incorporates a ground wire 96. The smaller diameter wire provides added likelihood that a single point ground results upon immersion of the probe. Also best seen in FIG. 7 are additional details of probe 70. See, for example, pins 60 and 62 of cap 17. Also shown is a temporary combustible paper cap 50. Details of thermocouple connectors 92 and 94 are also seen as are plastic clip thermocouple assembly fixture 115 which serves to secure the thermocouple quartz tube and lead wires 24 and 26 during manipulation of the probe assembly. The porous baked probe body 72 enables flow of gases into and through the probe 70 upon immersion into the melt. The proximal ends of connecting wires 24 and 26 are adapted to interconnect with connector leads of known design. Internal wires in the probe may be bare if separated or selectively insulated in areas to prevent shorting.

Additional details of the internal configuration and wiring of the measuring devices can also be best seen in FIG. 7. Wires 26 and 24 are formed with flattened ends 92 and 94. Welds 99 and 100 secure thermocouple lead wires 97 and 98, respectively, at the cold junctions of thermocouple assembly. The base of quartz U-tube 16 is sealed by heat resistant sealants 101 and 103 in order to protect the interior of the U-tube 16 from the entry of contaminants during baking of the sand-resin body 72. It will be noted that, in a radical departure from previous devices, that the thermocouple cold junction areas and leads 97, 98, leads 92, 94 and welds 99 and 100 along with the other described internal electrical parts are all not shielded, are unprotected and thus are exposed and open to changes in gas pressure and therefore to the resultant gas flows.

Figure 8:
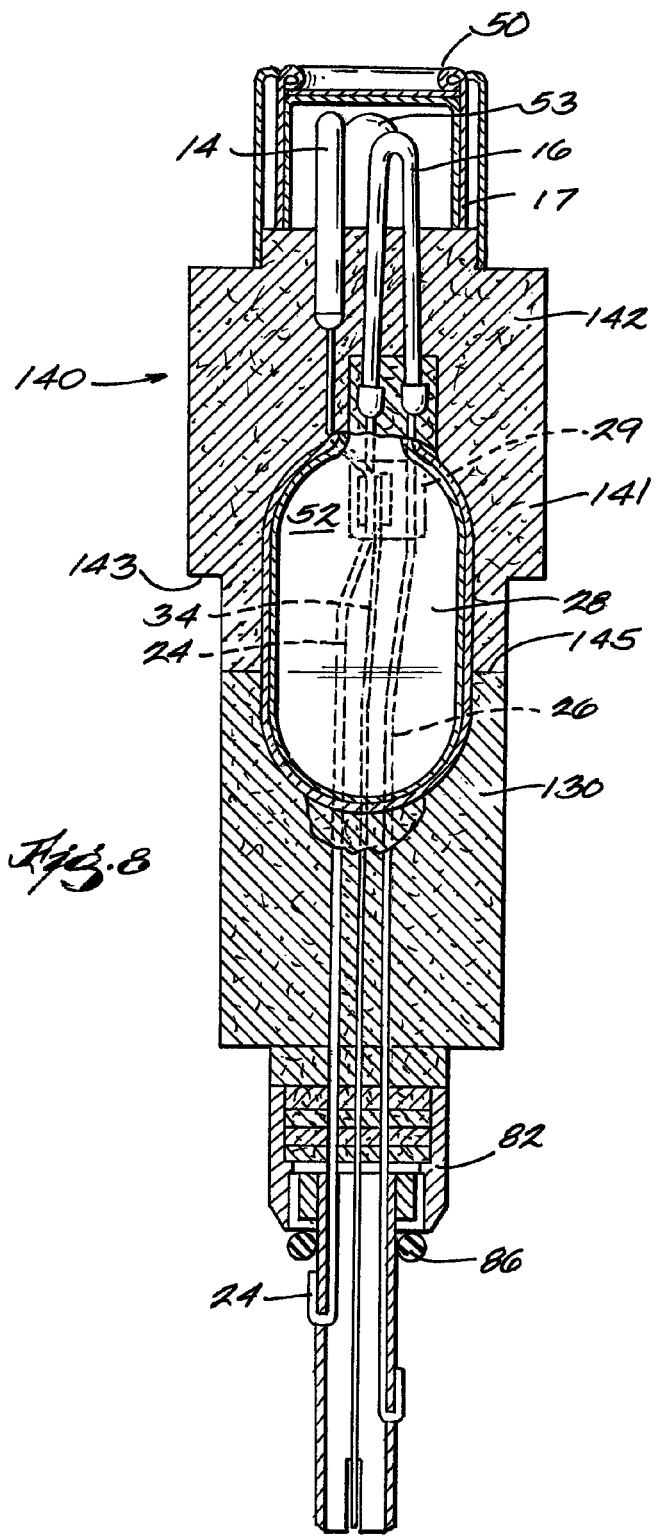
FIG. 8 is a longitudinal sectional view of a probe according to yet another embodiment which provides improved break-away characteristics to a sampling mold wherein hidden parts are shown by means of phantom lines.

Referring to FIG. 8, there is seen a modified probe 140 in accordance with the invention which includes a sampling mold 28. By positioning of mold 28 so it protrudes toward the probe immersion end, the ease of removal of the mold from the probe body is facilitated, thus desirably enhancing the speed of removal of a sample from within the mold cavity. The components of probe 140 indentified by the same identifying numerals used in the earlier described embodiments are the same as in those embodiments. As seen, sand-resin components 130 and 141 are formed around mold body 28, but are of differing compositions. A fault line 145 forms at the interface between these differing compositions. Thus, it has found that striking of the probe after removal of a metal sample from molten metal often causes the sand-resin to break along the fault line existing between the components 130 and 141. As in the earlier described embodiments, the portion 141 of the sand-resin body closest to the immersion end contains iron oxide, which imparts a darker color to that portion compared to lighter colored portion 130 that does not contain iron oxide. In a preferred embodiment, the portion 141 contains particles primarily of 70 to 90 mesh size while portion 130 primarily contains particles of 35 to 50 mesh size.

Probe 140 is provided with a flange area 142 having a greater length than the previous embodiments. This allows placement of mold 28 further toward the immersion end of the probe body, facilitating easier sample removal. A large paper capping, not shown, can be covering the immersion end to enhance the appearance of the finished probe. Also, a plastic plug 82 that contains internal vent channels can be molded directly onto portion 130 of the sand-resin thus eliminating the need for intermediate connectors (like connector 78 of FIGS. 2-3).

The invention claimed is:

1. An immersible probe assembly for molten metals comprising:
   a gas permeable baked sand-resin body having an immersion end and an opposed connection end adapted for being supported by a support lance and containing a communication connector providing electrical communication between said probe and remotely located monitoring apparatus;
   at least one molten metal testing device supported in the immersion end of said body, said sand-resin body allowing unobstructed gas flow through said immersion end, through said body and through said connection end, whereby gases released from a molten metal during immersion of said immersion end can enter and escape from within said probe through said connection end,
   a tube supporting the connection end, the end of said tube engaging a diametrically enlarged part of said sand-resin body which serves as a stop that limits the position of said tube relative to said immersion end, and
   a metal sampling mold embedded in said sand-resin body, a main body of said sampling mold being at least in part located in a part of said sand-resin body that protrudes toward the immersion end beyond said stop, an interface between said connection and immersion ends of the gas permeable baked sand-resin body forming a fault line for fracture of said gas permeable baked sand-resin body, such that a metal sample is released from said metal sampling mold when said metal sampling mold is struck by a hard structure, wherein said metal sampling mold is removed after retrieval of the metal sample.

2. A probe according to claim 1 wherein the sand-resin material on the connection end primarily comprises sand particles of 70-85 mesh size or smaller and on the immersion end primarily comprises sand particles of 35-45 mesh size or larger.

3. A probe according to claim 1 wherein said mold has a sample cavity that extends at least ⅛ inch beyond said stop.

* * * * *